United States Patent [19]
Schubert et al.

[11] Patent Number: 5,504,197
[45] Date of Patent: Apr. 2, 1996

[54] DNA ENCODING NEUROTROPHIC GROWTH FACTORS

[75] Inventors: David R. Schubert, La Jolla; Wolfgang H. Fischer, Encinitas, both of Calif.

[73] Assignee: The Salk Institute for Biological Studies, La Jolla, Calif.

[21] Appl. No.: 34,245

[22] Filed: Mar. 22, 1993

Related U.S. Application Data

[63] Continuation-in-part of Ser. No. 590,359, Sep. 27, 1990, Pat. No. 5,202,428, which is a continuation-in-part of Ser. No. 541,276, Jun. 20, 1990, abandoned.

[51] Int. Cl.$^6$ .................. C07H 21/04; C12N 15/12; C12N 15/11; C12N 15/00
[52] U.S. Cl. .................. 536/23.5; 435/69.1; 435/240.1; 435/320.1; 935/23; 935/66
[58] Field of Search .................. 536/23.5; 435/320.1, 435/49.51, 240.1; 530/399

[56] References Cited

U.S. PATENT DOCUMENTS 5,202,428  4/1993  Schubert .................. 435/320.1

OTHER PUBLICATIONS

Barinyage *Science* 264:772–774 (1994).
Bowie et al. *Science* 247: 1306–10 (1990).
Burgess et al. *Ann Review Biochem* 58:575–606 (1989).
Berg *Ann Rev Neurosci* 7:149–170 (1984).
Watters, et al. *J. of Neurochem* 49(3):705–13 (1987).
Wagner, *J of Neuroscience* 6(1):61–67 (1986).
Heymanns et al. *Proc. Natl Acad Sci* 84:7758–62 (1987).

*Primary Examiner*—Garnette D. Draper
*Assistant Examiner*—Stephen Gucker
*Attorney, Agent, or Firm*—Pretty, Schroeder, Brueggemann & Clark; Stephen E. Reiter; Robert T. Ramos

[57] ABSTRACT

Neurotrophic growth factor proteins isolated from novel clonal cell lines grown in culture are mitogenic for fibroblasts and glial cells; some promote nerve cell survival and are prospectively useful in treating diseases such as Parkinson's and Alzheimer's which result in cell death in the nervous system, as well as in treating patients prone to epileptic seizures and patients suffering from trauma to the CNS. Certain of these proteins may be useful in nerve regeneration as well as in treating such diseases and injuries. Some are particularly useful in promoting lung development. These proteins are also useful in methods of treating a patient to promote nerve cell regeneration in degenerative eye diseases. The proteins can be topically applied in suitable compositions for wound-healing applications, and they can be administered parenterally to promote lung development and to treat patients afflicted with nerve damage and/or nerve disease.

7 Claims, 1 Drawing Sheet

DNA ENCODING NEUROTROPHIC GROWTH FACTORS

This invention was made with Government support under Grants DK-26741 and NS09658-22 awarded by the National Institutes of Health. The Government has certain rights in the invention.

This application is a continuation-in-part of U.S. patent application Ser. No. 07/590,359, filed Sep. 27, 1990, now U.S. Pat. No. 5,202,428, issued Apr. 13, 1993, which is a continuation-in-part of U.S. patent application Ser. No. 07/541,276, filed Jun. 20, 1990, now abandoned, both of which are incorporated herein by reference in their entirety.

This invention relates to proteins having mitogenic activities and methods of treatment using such growth factors. More particularly, the invention relates to proteins which are mitogenic to fibroblasts and glial cells and may promote nerve cell survival and induce nerve cell differentiation. The invention further relates to methods for treating nerve cell diseases and for stimulating lung development.

BACKGROUND OF THE INVENTION

Certain diseases such as Parkinson's and Alzheimer's are the result of cell death in the nervous system. Epileptic seizures also result in cell death. Proteins which cause the survival (and division) of cell types may be of use in treating these diseases as well as in promoting nerve regeneration.

A major cause of blindness is the proliferation of blood vessels into the neural retina (angiogenesis) and the death of photoreceptor cells (various diseases). It is possible that angiogenic protein molecules secreted by certain tumor cells derived from the retina are responsible for aberrant growth of blood vessels into the neural retina in diseases such as diabetic retinopathy. In addition, tumor cell lines from the central nervous system have been under investigation for some time, see, for example: Schubert et al., *Nature* Vol. 249:224–227 (May 1974) and Bottenstein et al., *P.N.A.S.* Vol. 76,1:514–517 (January 1979). Such lines are believed to secrete proteins that promote cell division and growth.

Consistent with the foregoing, identification of such proteins would be of substantial value. Such identification should lead to the characterization of such proteins by their amino acid sequences and eventually to the production of such proteins in significant quantities for adequate in vitro and in vivo biological testing, likely by using recombinant DNA methods for their production. Characterization permits the design of agonists and antagonists of such proteins, and antagonists can often be of considerable importance.

SUMMARY OF THE INVENTION

Neurotrophic growth factor proteins, isolated from tumor cell cultures, are provided. These proteins, or fragments thereof, are useful as immunogens for producing antibodies. In addition, these proteins are mitogenic with respect to fibroblasts and glial cells, may be highly angiogenic, and may be a potential cause of retinal blindness. The proteins described herein may also prolong the life of nerve cells in culture, and may be useful in promoting nerve cell survival in patients afflicted with diseases associated with the frequent occurrence of cell death in the nervous system. These same proteins may also induce nerve cell differentiation.

In addition, certain proteins are mitogenic with respect to astrocytes and Schwann cells. These proteins are generally considered to be useful in promoting wound-healing. The proteins described herein are also considered to be of therapeutic value in stimulating lung development in premature babies and like situations. Thus, there are provided methods of treatment of patients suffering from nerve cell diseases and methods for promoting lung development, particularly in premature infants. In addition, the protein sequence described herein can be used to prepare degenerate probes for use in probing a variety of genomic libraries to clone other members of the instantly claimed neurotrophic growth factor gene family.

Anti-neurotrophic growth factor protein antibodies are also provided. These antibodies are useful for diagnostic assays to determine levels of neurotrophic growth factor proteins described herein in a given sample. The antibodies can also be used to purify neurotrophic growth factor proteins. Moreover, these antibodies are considered therapeutically useful to counteract the biological effect of neurotrophic growth factor proteins in vivo.

Isolated DNA molecules encoding the above-described neurotrophic growth factor proteins are also provided. The DNA molecules described herein are useful for producing invention neurotrophic growth factor proteins, when incorporated into a variety of protein expression systems known to those of skill in the art. In addition, the DNA molecules are useful as probes for assaying for the presence and/or amount of a neurotrophic growth factor gene or mRNA transcript in a given sample. The DNA molecules described herein, and fragments thereof, are also useful as primers and/or templates in a PCR reaction for amplifying genes encoding the neurotrophic growth factors described herein.

BRIEF DESCRIPTION OF THE DRAWINGS

The Y-axis in the figures should be understood to represent counts per minute×$10^{-3}$ of tritiated thymidine incorporated into Swiss 3T3 fibroblast cells.

DETAILED DESCRIPTION OF THE PREFERRED EMBODIMENTS

In accordance with the present invention, three neurotrophic growth factor proteins having mitogenic activities have been isolated from cell cultures of various naturally occurring and artificially induced tumors. These three proteins are referred to hereinafter as Platelet Derived Growth Factor-Associated Protein (PAP), Schwannoma Derived Growth Factor (SDGF), and B49-Derived Growth Factor. These protein molecules, which are released into the culture media of the tumor cell cultures, are isolated by selection based upon their mitogenic activity. The bioassay employed for selection monitors the ability of the protein to promote the incorporation of tritiated thymidine into Swiss 3T3 cells and is described in detail by Baird et al. in *P.N.A.S.* Vol. 85:2324–2328 (April 1988). Briefly, testing is carried out using a culture of serum-starved 3T3 fibroblast cells which are incubated for 20 hours with the purified protein and then incubated for about 5 hours with radioactive [$^3$H]-thymidine. Substantial incorporation of [$^3$H]-DNA into the cell line is indicative of accelerated cell mitosis.

Following treatment by heparin-Sepharose affinity chromatography and by reverse phase, high performance, liquid chromatography (RP-HPLC) to achieve substantial purification, the purified protein fractions are subjected to electrophoresis on 15% acrylamide gels in 0.1% SDS, which usually produces several bands of protein on the resultant gels. Each band is then individually eluted and assayed for biological activity, again using the Swiss 3T3 cell bioassay. Thereafter, further characterization of isolated proteins which show such mitogenic activity is carried out to identify the structure of the proteins, and to determine other biological properties thereof.

Several substantially pure neurotrophic growth factor proteins isolated in the foregoing manner may be useful to promote nerve and glial cell survival, as well as cause the differentiation of embryonic cells to neurons. Moreover, one protein that was isolated and partially purified is angiogenic and may be a potential cause of the proliferation of blood vessels in the neural retina. Antibodies raised against such a protein antigen should be useful in preventing blindness from this particular condition. Biologically active polypeptide fragments of these proteins are also contemplated for use in the compositions and methods described herein.

Use of the phrase "substantially pure" or "isolated" in the present specification and claims as a modifier of DNA, RNA, polypeptides or proteins means that the DNA, RNA, polypeptides or proteins so designated have been separated from their in vivo cellular environment. As a result of this separation and purification, the substantially pure DNAs, RNAs, polypeptides and proteins are useful in ways that the non-separated, impure DNAs, RNAs, polypeptides or proteins are not.

As used herein, the term "biologically active", or reference to the biological activity of a neurotrophic growth factor protein, or polypeptide fragment thereof, refers to a polypeptide that is able to produce one of the functional characteristics exhibited by any of the neurotrophic growth factors described herein, e.g., in Example 2. In one embodiment, biologically active proteins are those that demonstrate mitogenic activity on central nervous system glial cells or fibroblasts. Such activity may be assayed by any method known to those of skill in the art including, but not limited to, the Swiss 3T3 in vitro assay described by Baird et al., supra.

Of the substantially pure proteins isolated from tumor cell line cultures, three particular proteins have shown very substantial mitogenic properties for fibroblasts and are expected to be useful in wound-healing. One such protein also stimulates cell division in astrocytes and Schwann cells; another is highly mitogenic to glial cells, e.g. central brain glial cells and peripheral glial cells. The isolation and characterization of each of these neurotrophic growth factor proteins is described in detail hereinafter. Although it is possible to obtain these proteins by growing these cell lines, then isolating and purifying the proteins from the resulting culture medium, it is presently preferred to produce the proteins synthetically, either by chemical synthesis (if the length of the protein chain or subchain is such as to render chemical synthesis technically feasible) or, more preferably, by the use of recombinant DNA methods, which are presently well known in this art.

Presently preferred PAP neurotrophic growth factor proteins are those which have substantially the same amino acid sequence as the sequences set forth in Sequence ID Nos. 12 or 14, as well as functional, modified forms thereof. The presently most preferred PAP proteins are those which have the amino acid sequences set forth in Sequence ID Nos. 12 or 14.

As employed herein when referring to proteins or polypeptide fragments thereof, the term "substantially the same amino acid sequence" refers to amino acid sequences that will retain comparable functional and biological properties characteristic of the reference protein. In one embodiment, proteins having "substantially the same amino acid sequence" will have at least 70% identity with respect to the reference amino acid sequence, with adjustments being made for any gap caused by missing residue(s) in accordance with standard practices for comparison of protein sequences. In a preferred embodiment the proteins will have at least 75%, more preferably 90%, yet more preferably 95%, amino acid identity with respect to the reference amino acid sequence.

The protein(s) (polypeptides) disclosed herein can be subjected to various changes, substitutions, insertions, and deletions where such changes provide for certain advantages in use. The PAP or SDGF protein (or human homologs thereof) can be shortened either at the N-terminus or at the C-terminus or at both, without losing substantial biological activity for the purposes described hereinbefore, and such C-terminally and/or N-terminally shortened fragments are considered to be equivalents. For example, the SDGF protein might be shortened to a 79-residue protein in the form of residues 97–175. By N-terminally shortened, for example, it is meant that a sequence comprising one or more residues beginning at the N-terminus is deleted from the amino acid sequence of the peptide that is stated herein. Moreover, the SDGF or PAP protein might also be N-terminally extended without detrimental biological effect.

As another example, those of skill in the art recognize that numerous residues of the sequence presented in Sequence ID Nos. 12 and 14 can be conservatively substituted with other, chemically, sterically and/or electronically similar residues without substantially altering the biological activity of the resulting receptor species.

Examples of conservative substitutions include the substitution of one non-polar (hydrophobic) residue (such as isoleucine, valine, leucine or methionine) for another, the substitution of one polar (hydrophilic) residue for another (such as between arginine and lysine, between glutamine and asparagine, between glycine and serine, and the like), the substitution of one basic residue (such as lysine, arginine or histidine) for another, or the substitution of one acidic residue (such as aspartic acid or glutamic acid) for another. The phrase "conservative substitution" also includes the use of a chemically derivatized residue in place of a non-derivatized residue provided that such polypeptide displays the requisite binding activity.

"Chemical derivative" refers to a polypeptide having one or more residues chemically modified by reaction of a functional side group. Such derivatized molecules include, for example, those molecules in which free amino groups have been converted into amine hydrochlorides, p-toluene sulfonyl groups, carbobenzoxy groups, t-butyloxycarbonyl groups, chloroacetyl groups, formyl groups, and the like. Free carboxyl groups may be derivatized, for example, to form salts, methyl and ethyl esters or other types of esters or hydrazides. Free hydroxyl groups may be derivatized, for example, to from O-acyl or O-alkyl derivatives. The imidazole nitrogen of histidine may be derivatized to form N-im-benzylhistidine. Also contemplated as chemical derivatives are peptides which contain one or more naturally occurring amino acid derivatives of the twenty standard amino acids.

For example: 4-hydroxyproline may be substituted for proline; 5-hydroxylysine may be substituted for lysine; 3-methylhistidine may be substituted for histidine; homoserine may be substituted for serine; ornithine may be substituted for lysine, and the like. Polypeptides of the present invention also include polypeptides having one or more additions and/or deletions of residues relative to the sequence of a polypeptide whose sequence is shown herein, so long as the requisite biological activity is maintained.

Once a substantial portion of the amino acid sequence for one of the proteins of the present invention is known, cDNA corresponding to the protein of interest may be prepared. Briefly, messenger RNA (mRNA) is obtained from the respective cell line cultures which produced the protein of interest. A cDNA library or an expression library is produced in a conventional manner by reverse transcription from messenger RNA (mRNA) obtained from the appropriate cell line. By inserting such cDNA into cloning vectors, which are then used to transform a suitable host, the cDNA library is created. To select cDNA clones coding for desired protein of interest, hybridization probes (preferably mixed probes to accommodate the degeneracy of the genetic code) corresponding to likely unique portions of the protein are produced and used to identify clones containing such sequences. Next, cDNA is excised from the selected clones and inserted into suitable phage for subcloning and sequence analysis as is well known in this art.

In a preferred embodiment, cDNA encoding the PAP proteins disclosed herein have substantially the same nucleotide sequence as nucleotides 49–591 of SEQ ID NO:11 or nucleotides 22–564 of SEQ ID NO:13. The presently most preferred cDNA molecules encoding the PAP proteins have the same nucleotide sequence as nucleotides 49–591 of SEQ ID NO:11 or the same nucleotide sequence as nucleotides 22–564 of SEQ ID NO:13.

As employed herein, the term "substantially the same nucleotide sequence" refers to DNA having sufficient homology to the reference polynucleotide, such that it will hybridize to the reference nucleotide under typical stringency conditions employed by those of skill in the art. In one embodiment, DNA having substantially the same nucleotide sequence as the reference nucleotide encodes substantially the same amino acid sequence of SEQ ID NO:12 or SEQ ID NO:14. In another embodiment, DNA having "substantially the same nucleotide sequence" has at least 60% homology with respect to the nucleotide sequence of the reference DNA fragment with which the subject DNA is being compared. In a preferred embodiment, the DNA has at least 70%, more preferably 90%, yet more preferably 95%, homology to the comparative nucleotide sequence.

Alternatively DNA libraries may be screened by an immunological expression assay with an antibody raised against the protein of interest. Screening of the expression library with antibodies raised against the protein of interest may also be used, alone or in conjunction with hybridization probing, to identify or confirm the presence of the sought-after DNA sequences in DNA library clones. Such techniques are taught, for example, in Maniatis et al., *Cold Spring Harbor Laboratory Manual*, Cold Spring Harbor, N.Y. (1982), (hereinafter CSH).

Because mitogenic proteins from different mammalian species usually show high homologies, i.e., porcine, human, bovine, ovine and rat, such homologous mitogens from other species can be deduced using the same probes as were employed in searching the rat cDNA libraries. Alternatively, cDNA fragments of the gene sequence coding for the rat mitogen (or the entire sequence) can be used to probe the cDNA library of another species, e.g., human (see Example 1). Thus, the knowledge of the sequence of the rat mitogen allows the present-day molecular biologist to obtain the sequences of the mitogens of other mammalian species (or even nonmammalian species having a homologous protein) and to prepare such proteins by the use of recombinant DNA technology.

Because the mitogenic neurotrophic growth factor proteins of the present invention are relatively long chain peptides, synthesis by recombinant DNA techniques is the synthetic method of choice, as opposed to standard chain elongation procedures involving step-wise addition of amino acid residues. Accordingly, once an appropriate protein-encoding DNA chain is obtained, e.g., by oligonucleotide synthesis or by probing a cDNA library, as described hereinafter in Examples 1 and 2, synthetic DNA is then inserted into a cloning vector, being appropriately placed therein so as to ensure its expression when the recombinant cloning vector is introduced into an organism or cell line.

Double-stranded DNA encoding the protein of interest is constructed or modified with insertion into a particular appropriate cloning vector in mind. Preferably DNA uninterrupted by introns, i.e., cDNA, is employed. The cloning vector that is to be utilized to incorporate the DNA is selected appropriate to its viability and expression in a particular host organism or cell line. The manner of insertion of the DNA depends upon factors particular to the host; for example, if the DNA is to be inserted into a vector for transformation into a prokaryotic cell, such as *E. coli*, the DNA will be inserted 3' of a promoter sequence, a Shine-Delgarno sequence (or ribosome binding site) that is within a 5' non-translated portion and an ATG start codon. The cloning vector also provides a 3' non-translated region and a translation termination site.

For transfection into a eukaryotic cell, such as a yeast cell or a cell line obtained from a higher animal, e.g., Chinese hamster ovary cells, monkey kidney cells, human liver cells, rat hepatoma cells, TR1 cells and the like, the oligonucleotide sequence encoding the protein of interest is appropriately spaced from a capping site and in correct reading frame with respect to an ATG start signal. The cloning vector should also provide a 3' non-translated region and a translation termination site.

Prokaryotic transformation vectors, such as pBR322, pMB9, Col E1, pCR1, RP4 and lambda-phage, are available for insertion of DNA of the length which encodes the protein of interest with substantial assurance of at least some expression of the encoded polypeptide. Typically, such vectors are constructed or modified to have unique restriction site(s) appropriately positioned relative to a promoter, such as the lac promoter. Other suitable vectors and promoters are disclosed in detail in U.S. Pat. No. 4,798,885, issued Jan. 17, 1989, the disclosure of which is incorporated herein by reference in its entirety. The DNA chain may be inserted with appropriate linkers into such a restriction site, with substantial assurance of production in a prokaryotic cell line transformed with the recombinant vector. To assure proper reading frame, linkers of various lengths may be provided at the ends of the mitogen-encoding sequences. Alternatively, cassettes, which include sequences, such as the 5' region of the lac Z gene (including the operator, promoter, transcription start site, Shine-Delgarno sequence and translation initiation signal), the regulatory region from the tryptophan gene (trp operator, promoter, ribosome binding site and translation initiator), and a fusion gene containing these two promoters called the tap-lac or commonly called the Tac promoter, are available into which synthetic DNA may be conveniently inserted before the cassette is inserted into a cloning vector of choice.

Similarly, eukaryotic transformation vectors, such as the cloned bovine papilloma virus genome, the cloned genomes of the murine retroviruses, and eukaryotic cassettes, such as the pSV-2 gpt system [described by Mulligan and Berg, *Nature* Vol. 277:108–114 (1979)] the Okayama-Berg cloning system [*Mol. Cell Biol.* Vol. 2:161–170 (1982)], and the expression cloning vector described by Genetics Institute [*Science* Vol. 228:810–815 (1985)], are available which provide substantial assurance of at least some expression of the protein of interest in the transformed eukaryotic cell line.

For example, the gene segment encoding the SDGF mitogenic protein, following amplification, might be inserted into the plasmid pYEp, a shuttle vector which can be used to transform both *E. coli* and *Saccharomyces cerevisiae* yeast. Insertion of the synthetic DNA at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by radioimmunoassay (RIA) to be reactive with antibody raised against the SDGF protein, demonstrating that a polypeptide containing such polypeptide segments is being expressed within the yeast cells. After sufficient growth has been achieved, the mitogenic protein can be recovered from the supernatant using the RP-HPLC purification process described hereinbefore.

An expression vector may also be prepared that places a gene segment obtained from the cDNA shown in SEQ ID NOs 11 or 13 under the control of SV40 promoter [Gorman et al., *DNA Protein Engin. Tech.*. Vol. 2:3–10 (1990)] using the expression plasmid pCIS2 and introduced into the 293 human kidney cell line using the calcium phosphate coprecipitation method. The growth-conditioned medium of such transfected 293 human kidney cells revealed mitogenic activity for both Swiss 3T3 cells and primary astrocytes, showing that the mature protein of interest is expressed.

Antibodies of the present invention are readily produced by immunizing a mammal with an inoculum containing a neurotrophic growth factor protein (or polypeptide fragment thereof) of the invention, thereby inducing in the mammal the production of antibody molecules having immunospecificity for a particular neurotrophic growth factor (or polypeptide fragment thereof). For example, antibodies raised in rabbits against a synthetic peptide recognize the synthetic peptide and the neurotrophic growth factor from which the synthetic peptide is derived on an equimolar basis. Such antibodies are, therefore, capable of inhibiting the activity of the native protein in vitro.

As a specific example, antibodies to a particular neurotrophic growth factor may be obtained by immunizing three month old male and female white New Zealand rabbits with a synthetic neurotrophic growth factor peptide antigen to which Tyr has been added at the C-terminus. This C-terminus modification allows the neutrotropic growth factor antigen to be coupled to BSA by a bisdiazotized benzidine(BDB) linkage by reaction with BSA for 2 hours at 4° C. The reaction mixture is dialyzed to remove low molecular weight material, and the retentate is frozen in liquid nitrogen and stored at −20° C. Animals are immunized with the equivalent of 1 mg of the peptide antigen according to the procedure of Benoit et al. *P.N.A.S. USA*, 79, 917–921 (1982). At four week intervals, the animals are boosted by injections of 200 µg of the antigen and bled ten to fourteen days later. After the third boost, antiserum is examined for its capacity to bind radioiodinated antigen peptide and then purified by CMC-ion exchange column chromatography. The antibody molecules are then collected from the mammal and isolated to the extent desired by well known techniques such as, for example, by using DEAE Sephadex to obtain the IgG fraction.

It has been determined that neurotrophic growth factor proteins are expressed at high levels in the lungs of newborn mammals. It is considered that the protein will likely have therapeutic value in stimulating lung development in premature babies and in children with incompletely developed lungs. In this respect, it is thought that the neurotrophic growth factor protein of the invention functions by stimulating surfactant synthesis. Such surfactants are a mixture of lipoproteins (chiefly lecithin and sphingomyelin) secreted by the great alveolar (type II) cells into the alveoli and respiratory air passages; they are believed to operate by reducing the surface tension of pulmonary fluids, thus contributing to the elastic properties of pulmonary tissue.

The peptides of the invention would of course be administered under the guidance of a physician. Invention peptides will typically be administered in the form of a pharmaceutical composition which would contain the peptide in conjunction with a conventional pharmaceutically-acceptable carrier. For treating newborn infants to stimulate lung development, or for the treatment of children with incompletely developed lungs, it is likely that the peptide would be administered intranasally as a part of a saline aerosol containing at least about 10 µg of the peptide per milliliter; however, it might also be administered intravenously or by another suitable parenteral route, as a part of an appropriate pharmaceutical formulation. Such compositions would contain an appropriate quantity of active material, determined by the weight of the patient, as is common in this art. Thus, the daily dosage would vary with the size and age of the infant or child being treated. For example, a daily dosage of between about 25 micrograms to about 75 micrograms of the peptide, per kilogram of body weight, might be injected into the amniotic fluid in the placenta for treatment of the unborn embryo, with somewhat higher dosages being administered on a daily basis to infants and young children.

As earlier indicated, the neurotrophic growth factor proteins of the invention are mitogenic for a wide variety of normal cultured cells derived from tissue originating from the mesoderm and from the nervous system. These include fibroblast cells, astrocytic glial cells, and cells derived from peripheral nerves, called Schwann cells; the PAP and SDGF mitogens have shown biopotency in stimulating division of all such cells. Thus, these proteins are considered useful for promoting in vitro growth of cultured cell lines, such as cell lines that have been transformed by recombinant DNA techniques to produce useful polypeptides; they are also considered to be therapeutically useful in wound-healing, and possibly in the healing of ulcers. The PAP and SDGF proteins and mammalian homologs thereof, such as the 78-residue human homolog of SDGF, are considered to be therapeutically useful to stimulate lung development. Moreover, these proteins have potential therapeutic applications in treating retinal diseases that result in death of nerve cells, CNS injuries where nerve regeneration is required and in treating neural degenerative diseases; they are also prospectively useful in treating diseases such as Parkinson's and Alzheimer's which result in cell death in the nervous system, in treating patients prone to epileptic seizures, as well as in treating various instances where there is trauma to the CNS.

Substantially pure synthetic proteins or the nontoxic salts thereof, combined with a pharmaceutically acceptable carrier to form a pharmaceutical composition, may be parenterally or locally administered to mammals, including humans, for example, intravenously, subcutaneously, intramuscularly, topically or orally, depending upon the particular application intended. Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate, and the like. Topical applications may utilize the protein together with certain carriers, binders and fillers, appropriately selected to create a gel or a lotion for the treatment of superficial lesions, surgical incisions, burns or the like, as well known in this art.

The required dosage will vary with the particular condition being treated, with the severity of the condition and with the duration of desired treatment. The peptides should be administered under the guidance of a physician, and pharmaceutical compositions will usually contain the peptide in conjunction with a conventional, pharmaceutically-acceptable carrier. For example, for wound-healing a standard composition might include the protein at a concentration of about 1–10 weight % with topical application being repeated, e.g. up to about 5 times per day. As healing progresses, compositions of more dilute form, e.g., about 0.05 to 0.5% and/or a reduced application schedule may be used. For other applications, concentrations as low as about 1 nanogram to 1 microgram/ml may be used. The proteins may also be used in timed-release systems.

If used to treat patients afflicted with diseases of the nervous system, the PAP or the SDGF protein, or human or other mammalian homologs thereof, would preferably be administered parenterally at appropriate daily doses based upon the weight of the patient and the particular affliction. For such treatment, the peptides would also be administered only under the guidance of a physician and as a part of a pharmaceutical composition in combination with a conventional pharmaceutically-acceptable carrier. Such a pharmaceutical composition for intravenous administration might contain an appropriate weight percent of the peptide in saline as is commonly employed in this general field, or it might be administered as a part of a timed-release system. The dosage administered will depend upon the particular affliction being treated, dosages may be employed ranging from about 10 micrograms to about 50 milligrams of the peptide per kilogram of body weight of the patient per day.

The invention will now be described in greater detail with reference to the following non-limiting examples.

EXAMPLES

Example 1

Preparation of Isolated Rat R33-derived Platelet Derived Growth Factor-Associated Protein (PAP)

Purification of PAP from Rat R33 cells:

A number of tumor cell lines were adapted to growth in cell culture; these cell lines were each cloned from single cells obtained from tumors that had been induced in newborn rat eyes with nickel subsulfide. Accordingly, each cell line is homogeneous, and each was given a separate number. The cell line designated R33 was found to produce mitogenic proteins which were isolated, purified and identified, as set forth immediately hereinafter.

Figure 1:
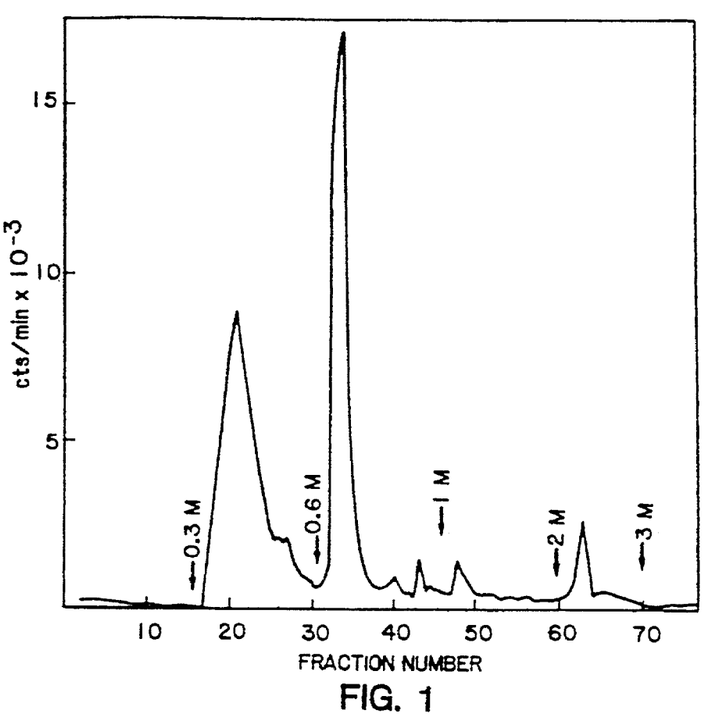
FIG. 1 shows the results of Swiss 3T3 biological assays of the fractions of R33 protein material separated by affinity chromatography using heparin-Sepharose and elution at a 5-step gradient of NaCl concentrations.

Approximately 2 liters of serum-free, growth-conditioned medium was collected from the R33 cell line, and was then passed through a 20 ml column of heparin-Sepharose (Pharmacia) which had previously been equilibrated with 10 mM Tris-HCl, at pH 7.4 and room temperature. The column was then washed sequentially with 0.01M Tris, pH 7.4 containing the following step gradients of salt: 0.3M, 0.6M, 1M, 2M and 3M NaCl. All of the fractions that were obtained were tested by the Swiss 3T3 cell bioassay described by Baird et al., Supra. The fractions eluting with the step using the 0.6M salt concentration were found to exhibit very substantial mitogenic activity using the Swiss 3T3 cell assay, the results of which assays for each of the individual fractions are plotted in FIG. 1, and one of the proteins is found to be highly angiogenic.

Figure 2:
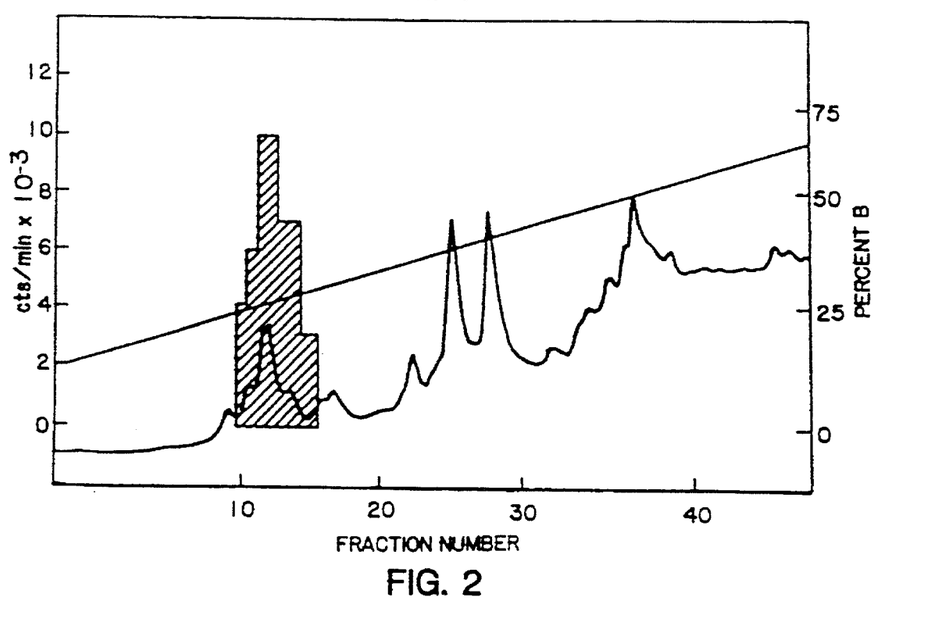
FIG. 2 shows purification of the peak of R33 protein obtained by the FIG. 1 separation, on an HPLC-RP $C_4$ column with elution via a gradient of acetonitrile in 0.1% trifluoroacetic acid over 3 hours, measuring optical density at 212μ.

The 0.6M fraction was then adjusted to a pH of 2, using trifluoroacetic acid (TFA), and pumped onto a Synchropak RP-4 $C_4$ (0.46×25 cm) reverse phase column having a 4000 angstrom particle size and a 300 angstrom pore size. Buffer A is 0.1% (v/v) TFA in water, and Buffer B is 1 ml TFA, 200 ml of water and 799 ml of acetonitrile. 0% Buffer B is used during the initial loading which is carried out at room temperature with a flow rate of about 1 ml/min. Following loading, a straight line gradient is begun in which the amount of Buffer B is uniformly and gradually increased from 0 to 80 volume % over 3 hours, as represented partially by the straight line in FIG. 2. Peaks of material exhibiting mitogenic activity elute at about 20% acetonitrile (as depicted by the cross-hatching in FIG. 2), and these peaks are pooled.

The pooled peaks are then subjected to gel electrophoresis. The purified protein material is exposed to 1% sodium dodecyl sulfate (SDS) at a pH of 6.8 at room temperature for about 30 minutes, and subsequently applied to a slab gel containing about 15% polyacrylamide (PAGE), as described by Laemmli, U. K., *Nature*, 227:680–685 (1970). Protein bands are visualized by silver staining. Several bands are formed, and each is individually eluted, then assayed for mitogenic activity. A single band of protein which migrates at about 26 kD (26 kilo Daltons or 26,000 molecular weight) contains all of the mitogenic activity; this protein is hereinafter referred to as Platelet Derived Growth Factor-Associated Protein (PAP).

The R33-derived PAP protein was, therefore, electrotransferred to nitrocellulose and subjected to in situ trypsinolysis. Tryptic peptides were separated by reversed phase HPLC on a Vydac C18 column. Three novel peptide sequences (SEQ ID NOs 4–6 of Table 1) were identified by automated Edman degradation. In addition, three peptides were found which were fragments of PDGF-A chain (SEQ ID NOs 1–3 of Table 1).

TABLE 1

Tryptic Peptide Sequences:

PDGF-A Fragments:

| SEQ ID NO: 1- | EVQVR |
| SEQ ID NO: 2- | VEYVR |
| SEQ ID NO: 3- | LEEHLE |

PAP Fragments:

| SEQ ID NO: 4- | QYTSPEEIDAQLQAEK |
| SEQ ID NO: 5- | VEGLIDIENPN(K) |
| SEQ ID NO: 6- | (A)LDES(TE) |

R33-derived Growth Factor Rat cDNA Preparation:

Based on the longest peptide of Table 1 (SEQ ID NO:4, 16 amino acids), oligonucleotide primers were designed and employed in a polymerase chain reaction (PCR) using cDNA obtained from the R33 cell line as a template. A λgt10 cDNA library was constructed using standard procedures. Poly A enriched RNA was obtained from R33 cells and reverse-transcribed. The cDNA was converted into double stranded DNA and NotI/EcoRI linker-adaptors were added. The DNA was then ligated into λgt10 DNA, packaged into phage particles, and amplified once.

Primers were designed, based on the N-terminal and C-terminal portion of SEQ ID NO:4, and used in a polymerase chain reaction using the R33 cDNA library described above as a template. The primers are shown in Table 2 as SEQ ID NOs: 7 and 8.

TABLE 2

PCR-Primers:

SEQ ID NO: 7- CA(G/C)TA(C/T)ACN(T/A)(G/C)NCC
SEQ ID NO: 8- (T/C)TT(C/t)TCNGC(T/C)TGNA(A/G)(T/C)TG
(N = G, A, T, C)

The resultant 48 bp amplification DNA product was subcloned into pGem 3Zf(−) and sequenced by the chain termination procedure. The amplification product was found to contain the correct sequence of five amino acids not encoded by the primers, in addition to the primer sequences.

An oligonucleotide corresponding to the central non-redundant portion of the PCR product was synthesized and, after end-labelling with $^{32}$P, used as a probe to screen the R33 cDNA library using well-known techniques described in Maniatis et al., *Molecular Cloning, A Laboratory Manual* (1982). Two positive clones were identified, isolated and sequenced. The resultant sequence is shown in SEQ ID NO:11. An open reading frame of 181 amino acids is identified. The initiator ATG sequence is preceded by a reasonable Kozak consensus sequence. Although the protein was secreted into growth medium, no typical N-terminal signal peptide sequence is present.

Cloning of Human cDNA:

The rat cDNA clone (SEQ ID NO:11) was used to generate a random labelled probe to screen a human retinal λgt11 cDNA library that was prepared by methods well known to those of skill in the art. Three positive human clones were obtained after three rounds of plaque purification. The longest clone was subcloned and sequenced, and was found to be truncated at the 5' end of the full length cDNA. In order to obtain a full length clone, an oligonucleotide corresponding to the 5' end of the rat cDNA clone was synthesized and used as a probe to rescreen the human library. Four positive human clones that were isolated were virtually identical to each other and corresponded in length to the rat cDNA clone. The sequence of the longest clone is depicted in SEQ ID NO:13. It is apparent that the sequences of both the DNA and the encoded protein are highly conserved between rat and human.

Northern Blot Assay to determine various tissues expressing the R33-derived Growth Factor gene:

A Northern blot of various newborn rat tissues was obtained employing well known techniques. Using a full-length rat cDNA clone (SEQ ID NO:11) as a probe, mRNA approximately 1.2 kb in length was detected in all tissues examined, except for liver. Thus mRNA which hybridizes to SEQ ID NO: 11 was detected in kidney, heart, muscle, intestine, lung, brain, and skin. The level of mRNA is highest in brain and lung.

Recombinant Expression of Rat R33-derived Growth Factor:

To obtain protein for biological testing, the coding region of the rat cDNA clone (SEQ ID NO:11, nucleotides 49–591) was subcloned into a bacterial expression plasmid, expressed and purified according to well known techniques. The expressed protein was assayed in a 3T3 cell mitogenicity assay in the presence and absence of PDGF. PDGF is a well-known protein dimer composed of two A chains (PDGF-A), two B chains (PDGF-B) or an A and B chain (PDGF-AB). It was found that PAP is a weak mitogen (1.2 fold stimulation over control). When PAP was assayed in the presence of a half-maximal dose of PDGF-A, it was found to enhance the effect of PDGF in excess of 2-fold.

EXAMPLE 2

Purification of Rat JS1-derived Growth Factor Protein:

Additional tumor cell lines are grown in culture, each cloned from single cells obtained from a spontaneous tumor that was found in a rat sciatic nerve generating a plurality of homogeneous (clonal) cell lines which appear to be a type indicative of Schwann cell origin. One cell line, arbitrarily marked JS1, was found to release more than one protein exhibiting mitogenic activity; however, only the protein of particular interest is hereinafter described. Inasmuch as the JS1 cell line has been identified as a Schwann cell line, the mature protein may be referred to as "SDGF" for Schwannoma derived growth factor.

Again, about 2 liters of serum-free, growth-conditioned JS1 cell medium is applied to a 20 ml column of heparin-Sepharose under the conditions described above, and similarly eluted using the same five-step gradient of varying NaCl concentrations. The protein fractions exhibiting mitogenic activity elute near the end of the step with the 0.6M salt concentration. These fractions are then adjusted to a pH of about 2 with TFA, and similarly pumped onto the $C_4$ reverse phase HPLC column described above, under the same conditions described above. Elution from the $C_4$ column is carried out as previously described using a uniform (straight line) gradient of about 10% to 70% acetonitrile (employing buffers A and B) over 3 hours. Optical density is continuously monitored at 212 nm. The protein material exhibiting mitogenic activity elutes in several peaks, one of which is at about 48% acetonitrile. Each of these peaks is then electrophoresed as described above.

In some instances, a single band of protein of about 32 kD is detected by the PAGE. This band exhibits mitogenic activity which is lost upon reduction with 2-mercaptoethanol. However, when the reduced material is subjected to electrophoresis, only a single band appears at about 32–35 kD, leading to the inference that the SDGF protein may be internally disulfide-linked or otherwise bonded to create a three-dimensional configuration that is lost when exposed to reducing conditions. When the protein material from HPLC-RP is run on 15% acrylamide gel containing 0.1% SDS and no reducing agent, a major broad band between about 31,000 and 35,000 Daltons is obtained. This band is cut into equal fractions that are then subjected to microsequencing. Some lower molecular weight bands between about 20 kD and 25 kD are also present. As a result of such microsequencing, it is believed that the N-terminal sequence of the proteins found in various of these fractions is identical. Thus, it is believed that these proteins are fragments of the same SDGF molecule, being C-terminally shortened versions of one another, i.e., shortened by the elimination of a peptide sequence beginning at the C-terminus.

The SDGF protein is also subjected to assays with astrocyte cell lines, with Schwann cells and with endothial cells. The protein is found to stimulate cell division of both astrocyte and Schwann cells; however, it does not appear to have any effect upon cell division of endothelial cells or of A431 human epidermoid carcinoma cells.

Based upon the known partial amino acid residue sequence, labelled oligonucleotides are synthesized for use as probes to detect corresponding cDNA. Because of the degeneracy of the genetic code, mixed hybridization probes are prepared and used. Two probe sets, based upon the amino-terminal amino acid residues 1–6 and 8–13 of SDGF, are synthesized and used to select, from such a cDNA library, cDNA clones that contain gene sequences encoding the mitogen of interest. Clones hybridizing with the probes were identified, and one that hybridized with both probe sets was purified.

As a result of sequence analysis of this selected clone, it is deduced that a SDGF precursor protein of 243 amino acids is encoded, which nucleotide and amino acid sequences are set forth in FIG. 6 of U.S. patent application Ser. No. 07/590,359, now U.S. Pat. No. 5,202,428, incorporated herein by reference. It is further concluded that this precursor results in the secretion of a mature protein in the form of a monomer, located 97 amino acid residues downstream from the initiation of the precursor protein.

This characterization is in agreement with the earlier analyses of the purified protein material obtained from the JS1 cell line. The indication is that the 19 N-terminal residues may be a signal sequence with the remaining 77 residues likely constituting part of a propeptide originally formed from the 243-residue precursor from which the mature SDGF protein is cleaved. The mature SDGF protein has a predicted molecular weight of 16,709 Daltons (assuming it includes the full length of 146 residues), and the disparity between the predicted molecular weight for this number of residues and the measured value of about 32 kD is believed due to glycosylation of the molecule. It is predicted that an N-linked carbohydrate is present at residue 103, and it is likely that O-linked glycosylation occurs at two or more sites in the mature SDGF protein.

The purified SDGF protein shows half maximal effectiveness in stimulating the cell division of fibroblasts at a concentration of about 15 picomolar. Based upon its similarity to murine EGF (epidermal growth factor), it is predicted that the mature protein contains three disulfide bridges between the cysteine residues in positions 137 and 150, 145 and 161, and 163 and 172, which locations are numbered with respect to the 243-residue precursor.

Characterization of SDGF (JS1) when applied in extracellular serum:

SDGF is an autocrine growth factor as well as a mitogen for astrocytes, Schwann cells and fibroblasts. Although SDGF was initially isolated from the Schwannoma cells as a mitogen for glial cells and fibroblasts, it has been found that SDGF causes the morphological and molecular differentiation of rat PC12 cells in a manner similar to, but distinguishable from NGF. SDGF also promotes PC12 survival in serum-free conditions. SDGF induced changes include neurite outgrowth and the induction of the mRNAs for both the GAP-43 and transin proteins, which are highly expressed in axons. In addition, both SDGF and NGF induce the transcription factor, NGF-A. The time course of the response to SDGF is similar to that for NGF. GAP-43 mRNA induction by both SDGF and NGF is inhibited by dexamethasone, but dexamethasone has no effect on NGFI-A mRNA synthesis. These observations show that SDGF has a differentiation and survival promoting effect on PC12 cells in addition to its mitogenic activity on glial cells and fibroblasts.

The above activities of SDGF are exerted when SDGF is applied extracellularly. Growth factors can function by either of two pathways. One is the paracrine pathway where secreted growth factors bind to the corresponding receptors of the target cells. Another is the autocrine pathway in which cells respond to the same growth factor they produce.

SDGF contains two basic amino acid clusters in the SDGF molecule which are homologous to SV40 T antigen nuclear targeting signal. Mutational analysis of these clusters showed that they function as nuclear targeting signals, and a gel retardation assay showed that SDGF binds to AT rich DNA sequences. CAT analysis showed that SDGF can bind to some promoters and act as a transcription factor. Both the wild type SDGF and a mutant defective in the nuclear targeting signals activate the immediate early genes NGFI-A and c-fos. The wild type SDGF is a mitogen for Swiss 3T3 fibroblast cells, but the mutant defective in the nuclear targeting signals is not mitogenic. Moreover, wild type SDGF potentiates $^3$H-thymidine incorporation in NIH 3T3 cells bearing an EGF receptor defective in the kinase domain, while the mutant SDGF does not stimulate DNA synthesis. These results show that transport into the nucleus is required for SDGF to induce a mitogenic response.

EXAMPLE 3

Purification of Rat B49-derived Growth Factor:

Tumors that were induced in newborn rats using nitrosoethylurea are used to create another series of cell lines which are grown in culture, each being cloned from a single cell obtained from such tumors, as described in Schubert et al., Supra. Molecules released into cell culture from one line arbitrarily marked as B-49, which cell line is believed to be of glial origin, were found to exhibit mitogenic activity.

Again, about 2 liters of serum-free, growth-conditioned cell medium from cell line B-49 is applied to a 20 ml column of heparin-Sepharose under the conditions described above, then similarly eluted using a five-step gradient of varying NaCl concentration. Four protein fractions exhibiting mitogenic activity elute at salt gradients of 0.3M, 0.6M, 1.0M and 3.0M. Each of these fractions is then adjusted to a pH of about 2, with TFA, and similarly pumped onto a $C_4$ reverse phase HPLC column as described above, under the same conditions described above. Elution from the $C_4$ column is carried out as previously described using a uniform gradient of about 0 to 70% Buffer B over 3 hours. A single peak exhibiting mitogenic activity elutes at about 30% acetonitrile for each of the four fractions, and each peak is then electrophoresed as described above. Several bands of protein are separated by PAGE for each fraction, and each is individually electroeluted and then assayed for mitogenic activity. A single band which migrates at about 22 kD (22,000 molecular weight) contains all proteins which exhibit mitogenic activity. Subsequent testing of this protein material from each of the four fractions shows that its activity is lost upon reduction as a result of treatment with about 5% 2-mercaptoethanol. Subjecting the reduced material to electrophoresis results in a single band at about 11 kD, allowing the inference that protein is a dimer of two identical subunits, which individual subunits do not appear to be mitogenically active.

Purified protein from each of the four fractions is subjected to microsequencing which shows that the N-terminus of each appears to have the following amino acid sequence (SEQ ID NO:9): Ser-Ile-Glu-Glu-Ala. The longest N-terminal sequence was that obtained from the fraction which eluted at 0.6M NaCl; its sequence was (SEQ ID NO:10) Ser-Ile-Glu-Glu-Ala-Ile-Pro-Ala-Val-X-Lys-Thr-Arg-X-Val-Ile-Tyr-X- wherein X is likely to be Cys. It is believed that all four of the proteins may be portions of the same parent molecule, i.e., C-terminally shortened versions thereof, perhaps shortened versions of the protein PDGF (about 30 kD) or a different form of that molecule. PDGF stands for Platelet Derived Growth Factor and is described in detail in publications of Ross et all, *Cell* Vol. 46:155–169 (July 1986) and of Nister et al., *P.N.A.S.* Vol. 81:926–930 (February 1984).

Although the invention has been described with regard to its preferred embodiments, which constitute the best mode presently known to the inventors, it should be understood that various changes and modifications as would be obvious to one having ordinary skill in this art may be made without departing from the scope of the invention, which is set forth in the claims appended hereto.

---

What is claimed is:

1. An isolated DNA comprising a nucleotide sequence encoding a biologically active neurotrophic growth factor protein, wherein said protein has a molecular weight of about 26 kD, a heparin affinity domain, and is mitogenic to Swiss 3T3 cells, and wherein said DNA encodes a protein comprising the same amino acid sequence as residues 1–181 of SEQ ID NO:12 or residues 1–181 of SEQ ID NO:14.

2. A DNA according to claim 1, wherein said DNA does not contain interruptions by introns.

3. A DNA according to claim 1, wherein said DNA has the same nucleotide sequence as nucleotides 49–591 of SEQ ID NO:11 or nucleotides 22–564 of SEQ ID NO:13.

4. A recombinant DNA expression vector containing the DNA of claim 1.

5. The vector of claim 4, wherein said DNA is operatively associated with transcription regulatory elements capable of expressing the DNA in a eukaryotic or prokaryotic host cell transformed with said vector.

6. A recombinant DNA expression vector containing DNA encoding a neurotrophic growth factor protein having a molecular weight of about 26 kD, wherein said protein has a heparin affinity domain, is a mitogen to Swiss 3T3 cells, and wherein said protein comprises the same amino acid sequence as amino acids 1–181 of SEQ ID NO:12 or amino acids 1–181 of SEQ ID NO:14.

7. Recombinant host cells transformed with the vector of claim 4.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: protein     ( v ) FRAGMENT TYPE: internal     ( x i ) SEQUENCE DESCRIPTION: SEQ ID NO:1:

Glu  Val  Gln  Val  Arg
    1                      5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: protein     ( v ) FRAGMENT TYPE: internal     ( x i ) SEQUENCE DESCRIPTION: SEQ ID NO:2:

Val  Glu  Tyr  Val  Arg
    1                      5

( 2 ) INFORMATION FOR SEQ ID NO:3:

( i ) SEQUENCE CHARACTERISTICS:
        ( A ) LENGTH: 6 amino acids (B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:3:

Leu Glu Glu His Leu Glu
1               5

(2) INFORMATION FOR SEQ ID NO:4:

(i) SEQUENCE CHARACTERISTICS:
 (A) LENGTH: 16 amino acids
 (B) TYPE: amino acid
 (C) STRANDEDNESS: single
 (D) TOPOLOGY: linear (ii) MOLECULE TYPE: protein (v) FRAGMENT TYPE: internal (xi) SEQUENCE DESCRIPTION: SEQ ID NO:4:

Gln Tyr Thr Ser Pro Glu Glu Ile Asp Ala Gln Leu Gln Ala Glu Lys
1               5                   10                  15

(2) INFORMATION FOR SEQ ID NO:5:

(i) SEQUENCE CHARACTERISTICS:
 (A) LENGTH: 12 amino acids
 (B) TYPE: amino acid
 (C) STRANDEDNESS: single
 (D) TOPOLOGY: linear (ii) MOLECULE TYPE: protein (v) FRAGMENT TYPE: internal (xi) SEQUENCE DESCRIPTION: SEQ ID NO:5:

Val Glu Gly Leu Ile Asp Ile Glu Asn Pro Asn Lys
1               5                   10

(2) INFORMATION FOR SEQ ID NO:6:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: protein (v) FRAGMENT TYPE: internal (xi) SEQUENCE DESCRIPTION: SEQ ID NO:6:

Ala Leu Asp Glu Ser Thr Glu
1               5

(2) INFORMATION FOR SEQ ID NO:7:

(i) SEQUENCE CHARACTERISTICS:
 (A) LENGTH: 14 base pairs
 (B) TYPE: nucleic acid
 (C) STRANDEDNESS: single
 (D) TOPOLOGY: linear (ii) MOLECULE TYPE: DNA (genomic)

(xi) SEQUENCE DESCRIPTION: SEQ ID NO:7:

CASTAYACNW SNCC                                                                 14

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

YTTYTCNGCY TGNARYTG                                                              18

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: unknown     (ii) MOLECULE TYPE: protein     (v) FRAGMENT TYPE: N-terminal     (xi) SEQUENCE DESCRIPTION: SEQ ID NO:9:

Ser Ile Glu Glu Ala
1               5

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS: single
        (D) TOPOLOGY: unknown     (ii) MOLECULE TYPE: protein     (v) FRAGMENT TYPE: N-terminal     (xi) SEQUENCE DESCRIPTION: SEQ ID NO:10:

Ser Ile Glu Glu Ala Ile Pro Ala Val Xaa Lys Thr Arg Xaa Val Ile
1               5                   10                  15
Tyr Xaa (2) INFORMATION FOR SEQ ID NO:11:

(i) SEQUENCE CHARACTERISTICS:
        (A) LENGTH: 787 base pairs
        (B) TYPE: nucleic acid
        (C) STRANDEDNESS: double
        (D) TOPOLOGY: both     (ii) MOLECULE TYPE: cDNA     (ix) FEATURE:
        (A) NAME/KEY: CDS
        (B) LOCATION: 49..594
        (D) OTHER INFORMATION: /product="Rat R33 PDGF-associated
            protein"

(xi) SEQUENCE DESCRIPTION: SEQ ID NO:11:

TCGAATTCGC GGCCGCCGAC GGCCGCGCGT GCAGCCGCCG GAGCCGAG ATG CCT AAA     57
                                                                                                        Met Pro Lys
                                                                                                        1

GGA GGT AGA AAG GGA GGC CAT AAA GGC AGC GTG AGG CAG TAT ACA AGC     105

|       |       |       |       |       |       |       |       |       |       |       |       |       |       |       |       |     |
|-------|-------|-------|-------|-------|-------|-------|-------|-------|-------|-------|-------|-------|-------|-------|-------|-----|
| Gly   | Gly   | Arg   | Lys   | Gly   | Gly   | His   | Lys   | Gly   | Ser   | Val   | Arg   | Gln   | Tyr   | Thr   | Ser   |     |
|       |       | 5     |       |       |       | 10    |       |       |       | 15    |       |       |       |       |       |     |
| CCT   | GAG   | GAG   | ATC   | GAT   | GCC   | CAG   | CTA   | CAG   | GCT   | GAG   | AAG   | CAG   | AAG   | GCC   | AAC   | 153 |
| Pro   | Glu   | Glu   | Ile   | Asp   | Ala   | Gln   | Leu   | Gln   | Ala   | Glu   | Lys   | Gln   | Lys   | Ala   | Asn   |     |
| 20    |       |       |       |       | 25    |       |       |       |       | 30    |       |       |       |       | 35    |     |
| GAA   | GAA   | GAT   | GAA   | CAA   | GAA   | GAA   | GGT   | GGA   | GAT   | GGG   | GCT   | TCG   | GGT   | GAC   | CCC   | 201 |
| Glu   | Glu   | Asp   | Glu   | Gln   | Glu   | Glu   | Gly   | Gly   | Asp   | Gly   | Ala   | Ser   | Gly   | Asp   | Pro   |     |
|       |       |       |       | 40    |       |       |       |       | 45    |       |       |       |       | 50    |       |     |
| AAA   | AAG   | GAG   | AAG   | AAA   | TCT   | CTA   | GAC   | TCA   | GAT   | GAG   | AGT   | GAA   | GAT   | GAA   | GAT   | 249 |
| Lys   | Lys   | Glu   | Lys   | Lys   | Ser   | Leu   | Asp   | Ser   | Asp   | Glu   | Ser   | Glu   | Asp   | Glu   | Asp   |     |
|       |       |       | 55    |       |       |       |       | 60    |       |       |       |       | 65    |       |       |     |
| GAT   | GAC   | TAC   | CAG   | CAA   | AAG   | CGA   | AAA   | GGT   | GTG   | GAA   | GGG   | CTC   | ATT   | GAC   | ATT   | 297 |
| Asp   | Asp   | Tyr   | Gln   | Gln   | Lys   | Arg   | Lys   | Gly   | Val   | Glu   | Gly   | Leu   | Ile   | Asp   | Ile   |     |
|       |       | 70    |       |       |       |       | 75    |       |       |       |       | 80    |       |       |       |     |
| GAG   | AAC   | CCC   | AAC   | CGG   | GTG   | GCA   | CAG   | ACG   | ACT   | AAG   | AAG   | GTG   | ACA   | CAA   | CTG   | 345 |
| Glu   | Asn   | Pro   | Asn   | Arg   | Val   | Ala   | Gln   | Thr   | Thr   | Lys   | Lys   | Val   | Thr   | Gln   | Leu   |     |
|       | 85    |       |       |       |       | 90    |       |       |       |       | 95    |       |       |       |       |     |
| GAT   | CTG   | GAT   | GGG   | CCA   | AAG   | GAA   | CTT   | TCA   | AGG   | AGA   | GAA   | CGA   | GAA   | GAA   | ATA   | 393 |
| Asp   | Leu   | Asp   | Gly   | Pro   | Lys   | Glu   | Leu   | Ser   | Arg   | Arg   | Glu   | Arg   | Glu   | Glu   | Ile   |     |
| 100   |       |       |       |       | 105   |       |       |       |       | 110   |       |       |       |       | 115   |     |
| GAG   | AAG   | CAG   | AAA   | GCA   | AAA   | GAG   | CGC   | TAC   | ATG   | AAA   | ATG   | CAT   | TTG   | GCT   | GGG   | 441 |
| Glu   | Lys   | Gln   | Lys   | Ala   | Lys   | Glu   | Arg   | Tyr   | Met   | Lys   | Met   | His   | Leu   | Ala   | Gly   |     |
|       |       |       |       | 120   |       |       |       |       | 125   |       |       |       |       | 130   |       |     |
| AAG   | ACG   | GAG   | CAG   | GCC   | AAG   | GCT   | GAT   | CTC   | GCC   | CGG   | CTG   | GCA   | ATC   | ATC   | CGG   | 489 |
| Lys   | Thr   | Glu   | Gln   | Ala   | Lys   | Ala   | Asp   | Leu   | Ala   | Arg   | Leu   | Ala   | Ile   | Ile   | Arg   |     |
|       |       |       | 135   |       |       |       |       | 140   |       |       |       |       | 145   |       |       |     |
| AAA   | CAG   | CGG   | GAG   | GAA   | GCA   | GCA   | AGA   | AAG   | AAA   | GAA   | GAA   | GAG   | AGG   | AAA   | GCA   | 537 |
| Lys   | Gln   | Arg   | Glu   | Glu   | Ala   | Ala   | Arg   | Lys   | Lys   | Glu   | Glu   | Glu   | Arg   | Lys   | Ala   |     |
|       |       | 150   |       |       |       |       | 155   |       |       |       |       | 160   |       |       |       |     |
| AAA   | GAT   | GAC   | GCA   | ACT   | TTG   | TCA   | GGA   | AAA   | CGA   | ATG   | CAG   | TCG   | CTC   | TCC   | CTG   | 585 |
| Lys   | Asp   | Asp   | Ala   | Thr   | Leu   | Ser   | Gly   | Lys   | Arg   | Met   | Gln   | Ser   | Leu   | Ser   | Leu   |     |
|       | 165   |       |       |       |       | 170   |       |       |       |       | 175   |       |       |       |       |     |
| AAT   | AAG   | TAAGCTGGCC | TGTGGAGGAG | ATGCCGGGGG | AACTGGGCCG | TGCCGCCAGG |       |       |       |       |       |       |       |       |       | 641 |
| Asn   | Lys   |       |       |       |       |       |       |       |       |       |       |       |       |       |       |     |
| 180   |       |       |       |       |       |       |       |       |       |       |       |       |       |       |       |     |

| ACCTCTGCCA | TGTCTCACCC | ACTCTGTGCC | CTGCGCGCTG | CAGCAGCCCC | TACGGCCAGG | 701 |
| AGCCCCTACG | GCCTGGGGCC | TCCTCTTCAT | CTTGGCACAG | AAATTGTTCA | GGGGATGTGG | 761 |
| GGGGGGGGGG | GGGCGGCCGC | GAATTC     |            |            |            | 787 |

( 2 ) INFORMATION FOR SEQ ID NO:12:

( i ) SEQUENCE CHARACTERISTICS:
        ( A ) LENGTH: 181 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:12:

|       |       |       |       |       |       |       |       |       |       |       |       |       |       |       |       |
|-------|-------|-------|-------|-------|-------|-------|-------|-------|-------|-------|-------|-------|-------|-------|-------|
| Met   | Pro   | Lys   | Gly   | Gly   | Arg   | Lys   | Gly   | Gly   | His   | Lys   | Gly   | Ser   | Val   | Arg   | Gln   |
| 1     |       |       |       | 5     |       |       |       |       | 10    |       |       |       |       | 15    |       |
| Tyr   | Thr   | Ser   | Pro   | Glu   | Glu   | Ile   | Asp   | Ala   | Gln   | Leu   | Gln   | Ala   | Glu   | Lys   | Gln   |
|       |       |       | 20    |       |       |       |       | 25    |       |       |       |       | 30    |       |       |
| Lys   | Ala   | Asn   | Glu   | Glu   | Asp   | Glu   | Gln   | Glu   | Glu   | Gly   | Gly   | Asp   | Gly   | Ala   | Ser   |
|       |       | 35    |       |       |       |       | 40    |       |       |       |       | 45    |       |       |       |
| Gly   | Asp   | Pro   | Lys   | Lys   | Glu   | Lys   | Lys   | Ser   | Leu   | Asp   | Ser   | Asp   | Glu   | Ser   | Glu   |
|       | 50    |       |       |       |       | 55    |       |       |       |       | 60    |       |       |       |       |
| Asp   | Glu   | Asp   | Asp   | Asp   | Tyr   | Gln   | Gln   | Lys   | Arg   | Lys   | Gly   | Val   | Glu   | Gly   | Leu   |
| 65    |       |       |       |       | 70    |       |       |       |       | 75    |       |       |       |       | 80    |

```
Ile  Asp  Ile  Glu  Asn  Pro  Asn  Arg  Val  Ala  Gln  Thr  Thr  Lys  Lys  Val
                    85                       90                       95

Thr  Gln  Leu  Asp  Leu  Asp  Gly  Pro  Lys  Glu  Leu  Ser  Arg  Arg  Glu  Arg
               100                      105                 110

Glu  Glu  Ile  Glu  Lys  Gln  Lys  Ala  Lys  Glu  Arg  Tyr  Met  Lys  Met  His
               115                      120                 125

Leu  Ala  Gly  Lys  Thr  Glu  Gln  Ala  Lys  Ala  Asp  Leu  Ala  Arg  Leu  Ala
          130                      135                 140

Ile  Ile  Arg  Lys  Gln  Arg  Glu  Glu  Ala  Ala  Arg  Lys  Lys  Glu  Glu  Glu
145                      150                      155                      160

Arg  Lys  Ala  Lys  Asp  Asp  Ala  Thr  Leu  Ser  Gly  Lys  Arg  Met  Gln  Ser
               165                      170                 175

Leu  Ser  Leu  Asn  Lys
               180
```

( 2 ) INFORMATION FOR SEQ ID NO:13:

( i ) SEQUENCE CHARACTERISTICS:
        ( A ) LENGTH: 837 base pairs
        ( B ) TYPE: nucleic acid
        ( C ) STRANDEDNESS: double
        ( D ) TOPOLOGY: both     ( i i ) MOLECULE TYPE: cDNA     ( v i i ) IMMEDIATE SOURCE:
        ( A ) LIBRARY: Human neural retina     ( i x ) FEATURE:
        ( A ) NAME/KEY: CDS
        ( B ) LOCATION: 22..567
        ( D ) OTHER INFORMATION: /product="Human R33
                PDGF- associated protein"

( x i ) SEQUENCE DESCRIPTION: SEQ ID NO:13:

```
GAATTCCGCG  GCGGCGCCTC  A  ATG  CCT  AAA  GGA  GGA  AGA  AAG  GGA  GGC  CAC            51
                           Met  Pro  Lys  Gly  Gly  Arg  Lys  Gly  Gly  His
                            1              5                            10

AAA  GGC  CGG  GCG  AGG  CAG  TAT  ACA  AGC  CCT  GAG  GAG  ATC  GAC  GCG  CAG        99
Lys  Gly  Arg  Ala  Arg  Gln  Tyr  Thr  Ser  Pro  Glu  Glu  Ile  Asp  Ala  Gln
               15                      20                      25

CTG  CAG  GCT  GAG  AAG  CAG  AAG  GCC  AGG  GAA  GAA  GAG  GAG  CAA  AAA  GAA       147
Leu  Gln  Ala  Glu  Lys  Gln  Lys  Ala  Arg  Glu  Glu  Glu  Glu  Gln  Lys  Glu
               30                      35                      40

GGT  GGA  GAT  GGG  GCT  GCA  GGT  GAC  CCC  AAA  AAG  GAG  AAG  AAA  TCT  CTA       195
Gly  Gly  Asp  Gly  Ala  Ala  Gly  Asp  Pro  Lys  Lys  Glu  Lys  Lys  Ser  Leu
               45                      50                      55

GAC  TCA  GAT  GAG  AGT  GAG  GAT  GAA  GAA  GAT  GAC  TAC  CAG  CAA  AAG  CGC       243
Asp  Ser  Asp  Glu  Ser  Glu  Asp  Glu  Glu  Asp  Asp  Tyr  Gln  Gln  Lys  Arg
     60                      65                      70

AAA  GGC  GTT  GAA  GGG  CTC  ATC  GAC  ATC  GAG  AAC  CCC  AAC  CGG  GTG  GCA       291
Lys  Gly  Val  Glu  Gly  Leu  Ile  Asp  Ile  Glu  Asn  Pro  Asn  Arg  Val  Ala
75                      80                      85                      90

CAG  ACA  ACC  AAA  AAG  GTC  ACA  CAA  CTG  GAT  CTG  GAC  GGG  CCA  AAG  GAG       339
Gln  Thr  Thr  Lys  Lys  Val  Thr  Gln  Leu  Asp  Leu  Asp  Gly  Pro  Lys  Glu
               95                     100                     105

CTT  TCG  AGG  AGA  GAA  CGA  GAA  GAG  ATT  GAG  AAG  CAG  AAG  GCA  AAA  GAG       387
Leu  Ser  Arg  Arg  Glu  Arg  Glu  Glu  Ile  Glu  Lys  Gln  Lys  Ala  Lys  Glu
               110                     115                     120

CGT  TAC  ATG  AAA  ATG  CAC  TTG  GCC  GGG  AAG  ACA  GAG  CAA  GCC  AAG  GCT       435
Arg  Tyr  Met  Lys  Met  His  Leu  Ala  Gly  Lys  Thr  Glu  Gln  Ala  Lys  Ala
               125                     130                     135
```

| | | | | | | | | | | | | | | |
|---|---|---|---|---|---|---|---|---|---|---|---|---|---|---|
| GAC | CTG | GCC | CGG | CTG | GCC | ATC | ATC | CGG | AAA | CAG | CGG | GAG | GAG | GCT | GCC | 483 |
| Asp | Leu | Ala | Arg | Leu | Ala | Ile | Ile | Arg | Lys | Gln | Arg | Glu | Glu | Ala | Ala |
| 140 | | | | | 145 | | | | | 150 | | | | | |
| CGG | AAG | AAG | GAA | GAG | GAA | AGG | AAA | GCA | AAA | GAC | GAT | GCC | ACA | TTG | TCA | 531 |
| Arg | Lys | Lys | Glu | Glu | Glu | Arg | Lys | Ala | Lys | Asp | Asp | Ala | Thr | Leu | Ser |
| 155 | | | | | 160 | | | | | 165 | | | | | 170 |
| GGA | AAA | CGA | ATG | CAG | TCA | CTC | TCC | CTG | AAT | AAG | TAACTGCGAC | CCGTGGGAGG | 584 |
| Gly | Lys | Arg | Met | Gln | Ser | Leu | Ser | Leu | Asn | Lys |
| | | | | 175 | | | | | 180 | | | | | | |

```
AGATGCCGGG   GACCTGGGCC   GCGCTGCCAG   GACCTCTGCT   GTGTCTCGCC   CACCCTGTGC        644

CCTGGCGCCG   CTGCAACAGC   CCCTCATGGC   CAGGAGCCCC   CCATGCCTGG   GCCTCCTCTT        704

CATCTTGGCA   CAGAAATTGT   TTGGGGGATG   GGGGGGGGAC   TGGGGAGGG    GTAGCTGCTA        764

TCTTTGAGAC   AGAAAGATGC   AGGACAGCAT   TTCATATGTA   ACCATTTGAA   TGTTTTTGCT        824

GTTTTTAGAA   TTC                                                                  837
```

( 2 ) INFORMATION FOR SEQ ID NO:14:

( i ) SEQUENCE CHARACTERISTICS:
        ( A ) LENGTH: 181 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:14:

```
Met  Pro  Lys  Gly  Gly  Arg  Lys  Gly  Gly  His  Lys  Gly  Arg  Ala  Arg  Gln
 1              5                        10                       15

Tyr  Thr  Ser  Pro  Glu  Glu  Ile  Asp  Ala  Gln  Leu  Gln  Ala  Glu  Lys  Gln
              20                        25                  30

Lys  Ala  Arg  Glu  Glu  Glu  Glu  Gln  Lys  Glu  Gly  Gly  Asp  Gly  Ala  Ala
           35                       40                  45

Gly  Asp  Pro  Lys  Lys  Glu  Lys  Lys  Ser  Leu  Asp  Ser  Asp  Glu  Ser  Glu
      50                        55                  60

Asp  Glu  Glu  Asp  Asp  Tyr  Gln  Gln  Lys  Arg  Lys  Gly  Val  Glu  Gly  Leu
 65                  70                       75                       80

Ile  Asp  Ile  Glu  Asn  Pro  Asn  Arg  Val  Ala  Gln  Thr  Thr  Lys  Lys  Val
                 85                       90                       95

Thr  Gln  Leu  Asp  Leu  Asp  Gly  Pro  Lys  Glu  Leu  Ser  Arg  Arg  Glu  Arg
              100                      105                 110

Glu  Glu  Ile  Glu  Lys  Gln  Lys  Ala  Lys  Glu  Arg  Tyr  Met  Lys  Met  His
           115                      120                 125

Leu  Ala  Gly  Lys  Thr  Glu  Gln  Ala  Lys  Ala  Asp  Leu  Ala  Arg  Leu  Ala
      130                      135                 140

Ile  Ile  Arg  Lys  Gln  Arg  Glu  Glu  Ala  Ala  Arg  Lys  Lys  Glu  Glu  Glu
145                      150                 155                      160

Arg  Lys  Ala  Lys  Asp  Asp  Ala  Thr  Leu  Ser  Gly  Lys  Arg  Met  Gln  Ser
                 165                      170                 175

Leu  Ser  Leu  Asn  Lys
              180
```